United States Patent [19]
Jeppsson et al.

[11] Patent Number: 5,338,293
[45] Date of Patent: Aug. 16, 1994

[54] SET OF TUBES FOR PERITONEAL DIALYSIS

[75] Inventors: Jan-Bertil Jeppsson, Lomma; Ingvar Losell, Staffanstorp, both of Sweden

[73] Assignee: Gambro AB, Sweden

[21] Appl. No.: 62,326

[22] Filed: May 14, 1993

Related U.S. Application Data

[63] Continuation of Ser. No. 815,178, Dec. 31, 1991, abandoned.

[30] Foreign Application Priority Data

Feb. 18, 1991 [SE] Sweden .............................. 9100471-3

[51] Int. Cl.⁵ .............................................. A61M 1/00
[52] U.S. Cl. ........................................ 604/29; 604/30; 604/113
[58] Field of Search ................... 604/4, 6, 27–29, 604/43, 80, 82, 83, 113, 283, 284, 326, 411, 30

[56] References Cited

U.S. PATENT DOCUMENTS

| | | |
|---|---|---|
| Re. 32,303 | 12/1986 | Lasker et al. . |
| 1,960,417 | 5/1934 | Pair Jr. .................. 604/113 |
| 4,202,332 | 5/1980 | Tersteegen et al. ........... 604/284 |
| 4,252,115 | 2/1981 | Schael . |
| 4,416,280 | 11/1983 | Carpenter et al. .............. 604/4 |
| 4,636,204 | 1/1987 | Christopherson et al. . |
| 4,701,159 | 10/1987 | Brown et al. .................. 604/43 |
| 4,851,126 | 7/1989 | Shoendorfer .................. 604/6 |
| 4,935,004 | 6/1990 | Cruz . |

FOREIGN PATENT DOCUMENTS

| | | |
|---|---|---|
| 1125134 | 6/1982 | Canada .................. 604/80 |
| 0078565 | 10/1982 | European Pat. Off. . |
| 0243547 | 5/1986 | European Pat. Off. . |
| 0335814 | 1/1989 | European Pat. Off. . |
| WO8402277 | 6/1984 | PCT Int'l Appl. . |
| WO8606282 | 11/1986 | PCT Int'l Appl. . |
| 2009619 | 12/1978 | United Kingdom . |

*Primary Examiner*—John D. Yasko
*Assistant Examiner*—Anthony Gutowski
*Attorney, Agent, or Firm*—Lerner, David, Littenberg, Krumholz & Mentlik

[57] ABSTRACT

Tube sets are disclosed for peritoneal dialysis including a unitary tubular member having a number of lumens, including at least two lumens, the first for supplying fresh dialysis solution to the patient, and the second for discharging spent dialysis solution from the patient, such that the unitary tubular member can both supply the fresh dialysis solution and discharge the spent dialysis solution and at the same time heat can be transferred therebetween.

13 Claims, 3 Drawing Sheets

SET OF TUBES FOR PERITONEAL DIALYSIS

This is a continuation of application Ser. No. 07/815,178, filed on Dec. 31, 1991 (now abandoned).

FIELD OF THE INVENTION

The present invention relates to tube sets for use in connection with peritoneal dialysis. More particularly, the present invention relates to tube sets including a patient tube which is connectable to a patient conduit communicating with a patient's peritoneal cavity at one end and means for connecting a supply of fresh dialysis solution and for discharging spent dialysis solution from the other end.

BACKGROUND OF THE INVENTION

Peritoneal dialysis is quite well-known and, for a long time, has been found to be a proven alternative to hemodialysis for cleansing the blood of patients who have failing kidneys, or whose kidneys do not function at all.

Examples of various systems and devices which are intended for use in peritoneal dialysis can be found, for example, in European Patent No. 335,814; International Application No. WO 84/02277; British Patent No. 2,009,619; and U.S. Pat. Nos. Re. 32,203 and 4,252,115. In these systems, peritoneal catheters of the type which are described, for example, in International Application No. 86/06282 and U.S. Pat. No. 4,935,004 are utilized.

The various systems can then be connected to the peritoneal catheter by means of connectors, such as those described in U.S. Pat. No. 4,636,204.

Patient tubes of various lengths thus form a part of all of these systems, which tubes attach the patient's peritoneal catheter to the rest of the system. For the patient's comfort, these patient tubes are often provided with a length of from two to three meters. In this manner, each change of dialysis solution results in the return of a considerable amount of already used or spent dialysis solution.

SUMMARY OF THE INVENTION

In accordance with the present invention, these and other difficulties have now been overcome by the invention of a tube set for use in connection with peritoneal dialysis of a patient which includes a unitary tubular member having a first end and a second end, and containing a plurality of lumens including a first lumen and a second lumen, the first and second lumens being separated from each other, the first lumen at the first end of the unitary tubular member being connectable to supply means for fresh dialysis solution to be supplied to the patient, the second lumen at the first end of the unitary tubular member being connectable to discharge means for discharge of spent dialysis solution from the patient, and the second end of the unitary tubular member being connectable to patient conduit means for connection with the peritoneal cavity of the patient, whereby the unitary tubular member can both supply the fresh dialysis solution and discharge the spent dialysis solution from the patient and heat can be simultaneously transferred therebetween.

In accordance with one embodiment of the tube set of the present invention, the tube set includes first end connecting means for connection to the first end of the unitary tubular member, the first end connection means including a first channel for connection only to the first lumen of the unitary tubular member and a second channel for connection only to the second lumen of the unitary tubular member. Preferably, the first end connecting means has a T-connector including wall means separating the first channel from the second channel. In another embodiment the tube set includes fresh dialysis solution supply means connected to the first channel for supply of the fresh dialysis solution to the first lumen. Preferably, the first dialysis solution supply means includes bag connection means for connection to a bag for control of the amount of the fresh dialysis solution supplied to the patient.

In another embodiment, the first dialysis solution supply means includes fresh dialysis solution connection means for connection of the first lumen to a source of fresh dialysis solution. In yet another embodiment, the tube set includes spent dialysis solution discharge means connected to the second channel for discharge of the spent dialysis solution from the second lumen. Preferably, the spent dialysis solution discharge means includes bag connection means for connection to a bag for control of the amount of the spent dialysis solution discharged from the patient.

In accordance with another embodiment of the present invention, the tube set includes second end connecting means for connection to the second end of the unitary tubular member, the second end connecting means including common chamber means for fluid connection with both the first and second lumens.

In accordance with a preferred embodiment of the present invention, the tube set includes a plurality of lumens comprising more than two lumens, and preferably comprising four lumens, most preferably, a pair of first lumens and a pair of second lumens discussed above.

In accordance with another embodiment of the present invention the tube set includes a unitary tubular member which includes a partition wall dividing the unitary tubular member into the first and second lumens such that these lumens comprise symmetrical, semi-circular channels. Preferably, the unitary tubular member includes partition means dividing the unitary tubular member into a pair of first lumens and a pair of second lumens.

In accordance with the present invention, the above objects are thus achieved primarily by the use of a patient tube produced with a double lumen construction along at least a portion of its length, thus providing a first channel for the fresh dialysis solution and a second channel for the spent dialysis solution. While a preferred embodiment of the present invention includes a T-connector or the like at the first end of the unitary tubular member, the first end connecting means can also alternately employ a suitable valve construction or the like.

At the end of the patient tube which is adjacent to the patient, namely, the second end of the unitary tubular member, the two channels in the patient tube are caused to merge in or near the coupling arrangement at the end thereof. This is preferably achieved by the two channels opening into a common chamber which communicates with the patient tube which is, in turn, in communication with or connectable to the patient's peritoneal catheter.

As is further discussed above, in a preferred embodiment, the tube for discharge of spent dialysis solution is in communication with or is connectable to a bag or similar apparatus intended for control of the weight and/or volume of spent dialysis solution. In this embodiment, this tube also communicates with or is connectable to a bag or similar device intended for the collection of waste such that the spent fluid can be collected in a controlled manner and not freely released into a drain or the like.

In accordance with this invention, a simple and inexpensive design is provided if the patient tube is divided into two symmetrical, semi-circular channels by a partition wall. In this embodiment, efficient heat transfer is obtained between the spent dialysis solution and the fresh dialysis solution. Further improved heat transfer is achieved if the patient tube is divided into four symmetrical channels by two perpendicular partition walls. In such a design, two diagonally opposite channels can thus be used for the fresh dialysis solution, and the other two diagonally opposite channels for the spent dialysis solution. A further advantage of such a design is that the tube does not easily bend. As a consequence, the risk of blocking any of the channels by such bending or nicking is substantially reduced.

BRIEF DESCRIPTION OF THE DRAWINGS

In connection with the following detailed description, reference is made to the drawings in which.

DETAILED DESCRIPTION

Figure 1:
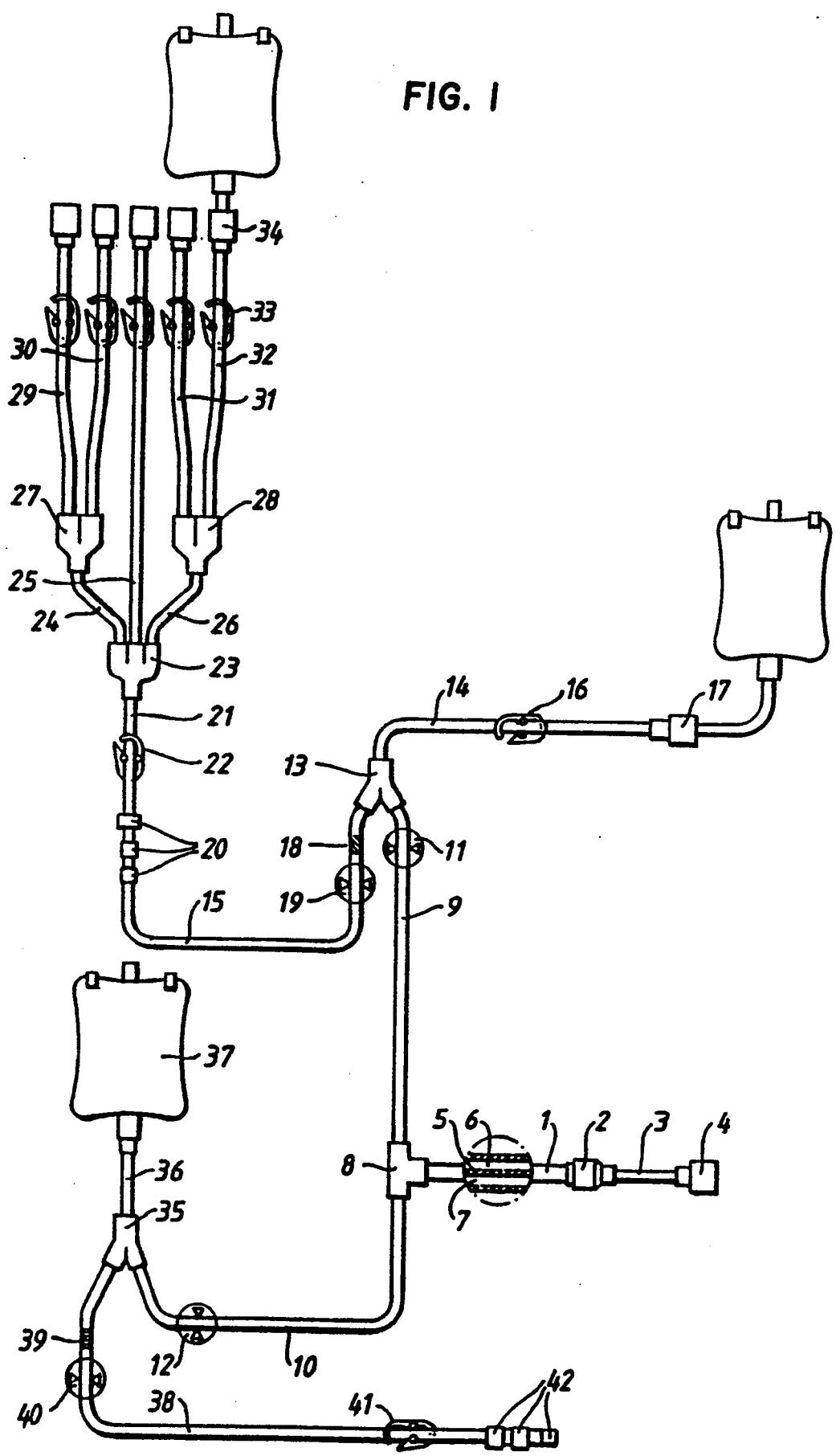
FIG. 1 is a front, elevational, perspective view of a tube set in accordance with the present invention connected to apparatus for use in peritoneal dialysis.

Referring to the Figures, in which like reference numerals refer to like portions thereof, referring first to FIG. 1, a preferred embodiment of the tube set in accordance with the present invention is shown therein.

In order to appreciate precisely how the various components can be constructed, reference is made to that which is generally known, for example, from the above-mentioned patents, namely, European Patent No. 335,814; International Application No. WO 84/02277; British Patent No. 2,009,619; and U.S. Pat. Nos. Re. 32,203 and 4,252,115, the disclosures of each of which are incorporated herein by reference thereto. The tube set shown in FIG. 1 consists of a patient tube 1 which, by means of a connector piece 2, communicates with a patient conduit 3, which, in turn, is connectable with the help of a connector arrangement 4 to a patient's peritoneal catheter. The patient tube (or unitary tubular member) 1 is divided into two channels by means of partition wall 5. That is, the patient tube 1 includes one channel 6 for fresh dialysis solution and one channel 7 for spent dialysis solution. At its end, which is distal from the patient, the patient tube 1 is connected by means of a T-connector 8 to both a tube 9 for the supply of fresh dialysis solution and to a tube 10 for the discharge of spent dialysis solution. The tube 9 can be closed off by means of a clamp arrangement 11 and, in the same way, the tube 10 can be closed of by means of a clamp arrangement 12. The tube 9 communicates with two tubes 14 and 15 by means of a Y-piece 13. the tube 14 is provided with a tube clamp 16, and terminates with a connector arrangement 17, which is adapted to be connected to a bag or similar device for control of the weight and/or volume of the supplied dialysis fluid.

The tube 15 is provided with a colored indication 18 (which can be colored green, for example), which is intended to simplify the attachment of the complete set of tubes to a dialysis monitor. From this indication 18, the tube 15 then extends through a clamp arrangement 19, and terminates with a connector arrangement 20, which permits connection to a tube 21, which is provided with a tube clamp 22. The tube 21 terminates with a connector piece 23, which provides for connection with three tubes 24, 25 and 26. The tubes 24 and 26 terminate, in turn, by means of Y-pieces 27 and 28, which, in turn, communicate with tubes 29, 30, 31 and 32. All of tubes 29, 30, 25, 31 and 32 are provided with tube clamps 33, and terminate with connector arrangements 34. Connector arrangements 34 are intended to be connected to different sources of fresh dialysis solution, for example, five bags containing said solution. In that manner, dialysis solution supply can be achieved by the force of gravity, i.e., by placing the bags at a suitable height, or by means of a suitable pump arrangement. In the example shown, five connector arrangements 34 are shown. In practice any number, such as from one to ten, can be utilized.

The tube 10 terminates with a Y-piece 35, which provides for connection to a tube 36, and to a bag 37. The bag 37 is intended to be used for control of the weight and/or the volume of spent dialysis fluid. The bag or the like can thus be placed on scales, for example. The tube 10, by means of the Y-piece 35, is also connected to a discharge tube 38 which is provided with a color marking 39 (which can be colored blue, for example), which has the same function as the color marking 18. The tube 38 extends from the color marking 39, by means of a clamp arrangement 40 and a tube clamp 41, to a connector arrangement 42, which is intended to connect the tube to a bag or similar device intended for the collection of waste.

Figure 2:
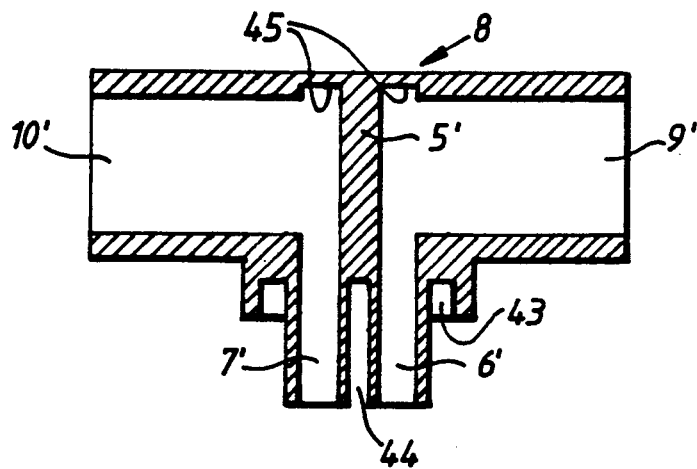
FIG. 2 is a top, elevational, sectional view of a T-connector for use in connection with the tube set of the present invention.
Figure 3:
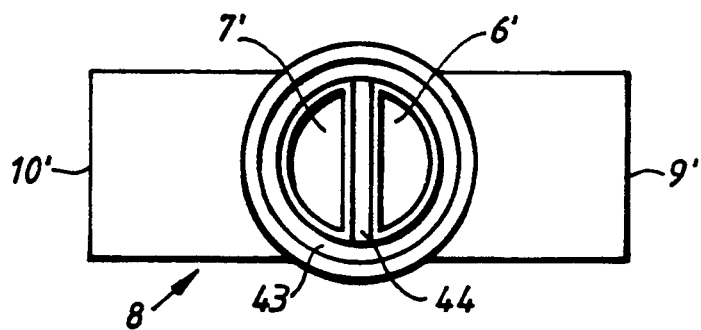
FIG. 3 is a front, elevational, perspective view of the T-connector shown in FIG. 2.

The T-connector 8 shown in FIGS. 1-3 can alternatively be formed as a Y-piece, for example. What is important is only that the inlets 9' and 10', which are intended to be connected to the tubes 9 and 10, respectively, are separated from each other by partition wall 5'. The semi-circular shaped channels 6' and 7' are both separated from each other, and each communicate with only one of the inlets 9' and 10', respectively. Reference numeral 43 denotes a ring-shaped channel, in which the patient tube 1 is intended to be inserted. At the same time, the partition wall 5 is adapted to be inserted into a slot 44. Reference numeral 45 denotes recesses from mold cores, which are necessary for formation of the channels 6' and 7'.

Figure 4:
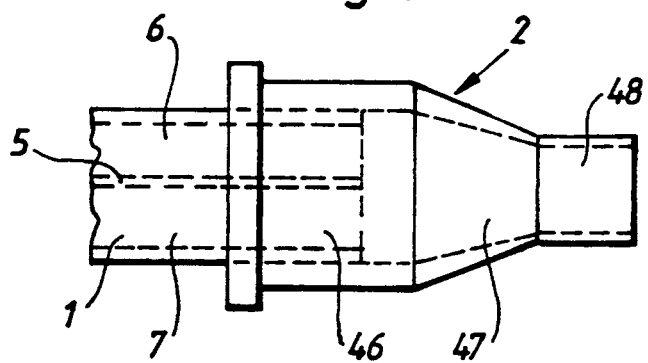
FIG. 4 is a side, perspective, partial view of a connector piece for use in connection with the tube set of the present invention.

Referring to FIG. 4, there is shown an example of how the connector piece 2 can be formed. A section of the patient tube 1 is shown in FIG. 4 inserted into a cavity 46, which leads into an open chamber 47. These two channels 6 and 7 are thus placed in open communication with chamber 47. By means of a connection nipple 48, this chamber thus communicates with the patient conduit 3, as shown in FIG. 1.

By means of this invention, only the small quantity of the spent dialysis solution which remains between the patient and the connector piece 2 is returned to the patient. Moreover, fresh dialysis solution is supplied by means of channel 6, and this solution is preheated, through partition wall 5, by the spent dialysis solution which is discharged through channel 7.

Figure 5:
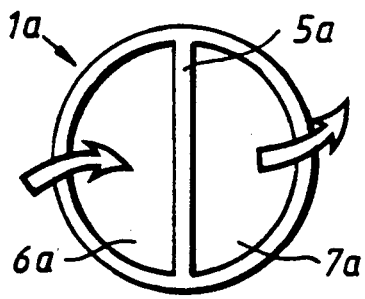
FIG. 5 is a front, sectional view of a patient tube in accordance with the present invention employing two semi-circular halves or channels.
Figure 6:
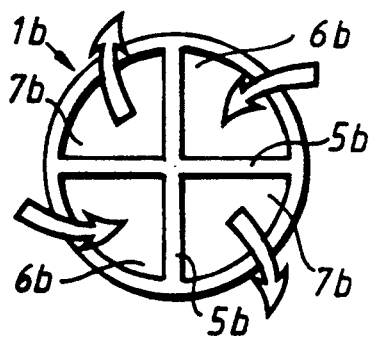
FIG. 6 is a front, elevational view of another patient tube in accordance with the present invention divided into four channels.
Figure 7:
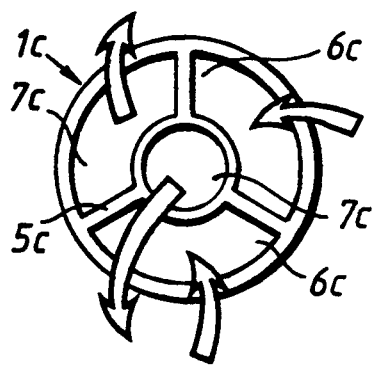
FIG. 7 is a front, sectional view of another patient tube in accordance with the present invention divided into four channels.

Referring next to FIGS. 5–7, there is shown therein sections through three different patient tubes in accordance with the present invention. These three tubes have been given the reference numerals 1a, 1b and 1c, respectively. The tube 1a is divided into two channels, 6a and 7a, by a partition wall 5a. In a similar manner, tube 1b is divided into four channels, 6b, 6b, 7b and 7b, by two perpendicularly arranged partition walls 5b. Finally, tube 1c is divided into four channels, 6c, 6c, 7c and 7c, by a modified arrangement of partition walls 5c. Tubes 1b and 1c have an advantage as compared to tube 1a in that they are more difficult to bend. Furthermore, the heat transfer between the spent dialysis solution and the fresh dialysis solution is improved in these two cases.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. By way of example, many of the components hereof can be modified in accordance with the above-mentioned patent publications. Alternatively, the two channels 6 and 7 can be formed as two concentrically arranged circular shaped channels, i.e., with an inner tube arranged centrally in an outer tube. In addition, the tube sets hereof can be complemented with further components if required, such as with a pump unit, for example, if it is desired to pump the various liquids.

We claim:

1. An apparatus including a tube set for use in connection with peritoneal dialysis of a patient having a peritoneal catheter with a single lumen, said apparatus comprising dialysis solution supply means for supplying fresh dialysis solution to the patient, supply tube means connected to said dialysis solution supply means for providing a flow path for said fresh dialysis solution, a unitary tubular member having a first end and a second end, said unitary tubular member containing a plurality of lumens including a first lumen and a second lumen and partition means separating said first lumen from said second lumen, both said first and second lumens and said partition means extending along substantially the entire length of said unitary tubular member, said first lumen at said first end of said unitary tubular member being connected to said supply tube means to provide a further flow path for the fresh dialysis solution to be supplied to the patient, second end connecting means connected to said second end of said unitary tubular member, said second end connecting means including a first end, a second end, and common chamber means for fluid connection with both said first and second lumens, said first end of said second end connecting means adapted for connection with said second end of said unitary tubular member, and said second end of said second end connecting means including a single lumen adapted to be connected to said peritoneal catheter of the patient, first discharge tube means connected to said second lumen at said first end of said unitary tubular member for transporting spent dialysis solution away from the patient, spent control bag means connected to said first discharge tube means for controlling the amount of spent dialysis solution discharged from the patient, and second discharge tube means connected to said spent control bag means for transporting the spent dialysis solution to a discharge location, whereby said unitary tubular member can both supply said fresh dialysis solution to the patient and discharge the spent dialysis solution from the patient and heat can be simultaneously transferred therebetween substantially along said entire length of said unitary tubular member.

2. The apparatus of claim 1 including first end connecting means for connection to said first end of said unitary tubular member, said first end connection means including a first channel for connection only to said first lumen of said unitary tubular member and a second channel for connection only with said second lumen of said unitary tubular member.

3. The apparatus of claim 2 wherein said first end connecting means comprises a T-connector including wall means separating said first channel from said second channel.

4. The apparatus of claim 1 wherein said fresh dialysis solution supply means includes bag connection means for connection to a bag for control of the amount of said fresh dialysis solution supplied to said patient.

5. The apparatus of claim 1 wherein said fresh dialysis solution supply means includes fresh dialysis solution connection means for connection of said first lumen to a source of said fresh dialysis solution.

6. The apparatus of claim 1 wherein said plurality of lumens comprises more than two lumens.

7. The apparatus of claim 6 wherein said plurality of lumens comprises four lumens.

8. The apparatus of claim 7 wherein said four lumens includes a pair of said first lumens and a pair of said second lumens.

9. The apparatus of claim 1 wherein said unitary tubular member includes a partition wall dividing said unitary tubular member into said first and second lumens, whereby said first and second lumens comprise symmetrical semicircular channels.

10. The apparatus of claim 8 including partition means dividing said unitary tubular member into said pair of said first lumens and said pair of said second lumens.

11. The apparatus of claim 1 wherein said unitary tubular member has a length of at least about 2 meters.

12. An apparatus including a tube set for use in connection with peritoneal dialysis of a patient, said apparatus comprising dialysis solution supply means for supplying fresh dialysis solution to the patient, supply tube means connected to said dialysis solution supply means for providing a flow path for the fresh dialysis solution, a unitary tubular member having a first end and a second end, said unitary tubular member containing a plurality of lumens including a first lumen and a second lumen and partition means separating said first lumen from said second lumen, both said first and second lumens and said partition means extending along substantially the entire length of said unitary tubular member, said first lumen at said first end of said unitary tubular member being connected to said supply tube means to provide a further flow path for the fresh dialysis solution to be supplied to the patient, second end connecting means connected to said second end of said unitary tubular member, said second end connecting means including a first end, a second end, and common chamber means for fluid connection with both said first and second lumens, said first end of said second end connecting means adapted for connection with said second end of said unitary tubular member, and said second end of said second end connecting means including a single lumen adapted to be connected to a peritoneal catheter of the patient, first discharge tube means connected to said second lumen at said first end of said unitary tubular member for transporting spent dialysis solution away from the patient, control means adapted to be connected to said first discharge tube means for controlling the amount of spent dialysis solution discharged from the patient, connector means having first, second and third ports for providing multiple passageways for transportation of the spent dialysis solution, said first port being connected to said first discharge tube means, said second port being connected to said control means, and said third port being connected to a second discharge tube means for transporting the spent dialysis solution to a discharge location, whereby said unitary tubular member can both supply said fresh dialysis solution to the patient and discharge the spent dialysis solution from the patient and heat can be simultaneously transferred therebetween substantially along said entire length of said unitary tubular member.

13. An apparatus including a tube set for use in connection with peritoneal dialysis of a patient, said apparatus comprising dialysis solution supply means for supplying fresh dialysis solution to the patient, supply tube means connected to said dialysis solution supply means for providing a flow path for the fresh dialysis solution, control bag means connected to said supply tube means for controlling the amount of fresh dialysis solution supplied to the patient, a unitary tubular member having a first end and a second end, said unitary tubular member containing a plurality of lumens including a first lumen and a second lumen and partition means separating said first lumen from said second lumen, both said first and second lumens and said partition means extending along substantially the entire length of said unitary tubular member, said first lumen at said first end of said unitary tubular member being connected to said supply tube means to provide a further flow path for the fresh dialysis solution to be supplied to the patient, second end connecting means connected to said second end of said unitary tubular member, said second end connecting means including a first end, a second end, and common chamber means for fluid connection with both said first and second lumens, said first end of said second end connecting means adapted for connection with said second end of said unitary tubular member, and said second end of said second end connecting means including a single lumen adapted to be connected to a peritoneal catheter of the patient, and discharge tube means connected to said second lumen at said first end of said unitary tubular member for transporting spent dialysis solution away from the patient to a discharge location, whereby said unitary tubular member can both supply said fresh dialysis solution to the patient and discharge the spent dialysis solution from the patient and heat can be simultaneously transferred therebetween substantially along said entire length of said unitary tubular member.

* * * * *